(12) United States Patent
Lambert et al.

(10) Patent No.: US 6,602,209 B2
(45) Date of Patent: Aug. 5, 2003

(54) METHOD AND DEVICE FOR ANALYZING ATHLETIC POTENTIAL IN HORSES

(75) Inventors: David H. Lambert, 2936 Trailside Dr., Lexington, KY (US) 40511; Deborah A. Boehler, Lexington, KY (US)

(73) Assignee: David H. Lambert, Lexington, KY (US)

( * ) Notice: Subject to any disclaimer, the term of this patent is extended or adjusted under 35 U.S.C. 154(b) by 0 days.

(21) Appl. No.: 09/927,806

(22) Filed: Aug. 10, 2001

(65) Prior Publication Data

US 2002/0123699 A1 Sep. 5, 2002

Related U.S. Application Data

(60) Provisional application No. 60/224,490, filed on Aug. 11, 2000.

(51) Int. Cl.$^7$ ............................... A61B 7/00; A61B 5/08
(52) U.S. Cl. .................... 600/586; 600/529; 128/897
(58) Field of Search .................... 600/300, 529, 600/532, 538, 586, 587, 595, 481; 128/897, 898; 119/700, 858, 174

(56) References Cited

U.S. PATENT DOCUMENTS

| | | | | |
|---|---|---|---|---|
| 4,774,679 A | * | 9/1988 | Carlin | 323/247 |
| 4,955,372 A | * | 9/1990 | Blackmer et al. | 128/203.16 |
| 5,737,280 A | * | 4/1998 | Kokubo | 235/377 |
| 5,782,240 A | | 7/1998 | Raviv et al. | |
| 6,168,568 B1 | | 1/2001 | Gavriely | |
| 6,228,037 B1 | * | 5/2001 | Derksen | 600/529 |
| 6,287,264 B1 | * | 9/2001 | Hoffman | 600/529 |

OTHER PUBLICATIONS

Attenburrow, "Respiratory Sounds recorded by Radio–Stethoscope from Normal Horses at Exercise," Equine Veterinary Journal (1978), 10 (3) 176–179.*
Belknap et al., "Failure of Subtotal Arytenoidectomy . . . " Am J Vet Res, vol. 51, No. 9, Sep. 1990.*
G. R. Barnes et al.; "Sound Spectrography in the Diagnosis of Equine Respiratory Disorders: A Preliminary Report" New Zealand Vet. J. (1979) vol. 27 pp. 145–146.
D. P. Attenburrow; "Time relationship between the respiratory cycle and limb cycle in the horse" Equine Vet. J. (1982) 14(1), 69–72.
H. Hornicke et al.; "Respiration in Exercising Horses"; Equine Exercise Physiology (198?) pp. 17–22.
D. P. Attenborrow; "Respiration and Locomotion" Equine Exercise Physiology, (1984) pp. 17–22.

(List continued on next page.)

Primary Examiner—Charles A. Marmor, II
(74) Attorney, Agent, or Firm—King & Schickli, PLLC

(57) ABSTRACT

Provided is a device for attachment to the head of a horse to enable recording of respiratory sounds in the intensely exercising animal, e.g., in a breezing Thoroughbred racehorse. Also provided are methods for predicting racing performance in a horse, e.g., a Thoroughbred race horse, comprising measuring expiratory and/or inspiratory times for a subject horse during exercise and relating such information to anatomy, front leg stance times and/or front leg stance distances and/or to speed (velocity) to determine the animal's potential to sustain a superior rate of ground coverage for a desired amount of time and identify a maximum comfortable velocity for the animal. A presently preferred embodiment of the methods of the invention comprises predicting performance via identification of expiratory time determined directly from the analysis of recorded respiratory sound from the exercising animal.

16 Claims, 5 Drawing Sheets

OTHER PUBLICATIONS

C. L. LaFortuna et al; "The Effects of Locomotor–Respiratory Coupling on the Pattern of Breathing in Horses" J. Physiol. (1996) Apr. 15;492(Pt2): 587–96 (Abstract).

S. Hobo et al.; "Characteristics of Respiratory Function During Swimming Exercise in Thoroughbreds" J. Vet.Med. Sci. (1998) Jun;60(6):687–9 (Abstract).

T. Art et al.; "Pulmonary Mechanics During Treadmill Exercise in Race Ponies" Vet. Res. Commun. (1988); 12(2–3):245–58 (Abstract).

S. Subburaj, L. Parvez, and T.G. Rajagopalan; "Methods of Recording and Analysing Cough Sounds" Pulmonary Pharmacology (1996) 9,269–279.

* cited by examiner

METHOD AND DEVICE FOR ANALYZING ATHLETIC POTENTIAL IN HORSES This application claims the benefit of priority in provisional application Ser. No. 60/224,490, filed on Aug. 11, 2000.

FIELD OF THE INVENTION

The present invention relates generally to the performance and athletic potential of horses. In particular, the present invention relates to a method or procedure to predict racing performance in a racehorse by measuring expiratory and inspiratory times during exercise. Most particularly, the present invention relates to a method of predicting racing performance by measuring expiratory and inspiratory times in galloping Thoroughbred racehorses.

BACKGROUND OF THE INVENTION

Literally for centuries man has sought the ability to predict athletic potential in performance animals. In particular, in the "sport of kings" (horse racing) horsemen are constantly in search of the superior racehorse and, accordingly, a consistent and reliable method to enable one to select the superior individual. There are numerous subjective factors to consider when evaluating an animal for future potential as a racehorse including, but not limited to e.g., pedigree, conformation and gait analysis, and the interrelationships thereof.

Oftentimes young horses are sold by commercial breeders or pinhookers and the like as future racing prospects. Would be owners frequently employ the services of individuals or "experts" (e.g., bloodstock agents) who specialize in their ability to select the superior individual. Given the enormous investment in time and money that is necessary to prepare and maintain a racing animal, e.g., a Thoroughbred racehorse or a racing Quarter Horse, horsemen are constantly in search of a reliable and reproducible and more objective method for selection of the potentially superior racing animal.

Many methods have been tried which utilize both phenotypic as well as genotypic characteristics, including, e.g., measuring the long bones of the distal extremities, measuring the size of the heart, measurement and anatomical consideration of the upper airway, dosage analysis of pedigree and the like. Although certain of these methods and/or various combinations thereof have found some degree of success, to date, there has not been a very consistent, reliable and reproducible system developed for analysis of athletic potential, especially wherein the method of analysis directly relates phenotypic characteristics, e.g., anatomy and/or biomechanical efficiency to the animal's ability to breathe during performance. Accordingly, there exists a need in the art for such a system.

It is generally known that, at the gallop, a horse must breathe in rhythm with his stride. The normal horse will usually take one breath with each stride and will normally breathe out or exhale only when his/her front legs are on the ground (i.e., during his/her front leg stance time). Prior to the present invention, however, the relationship between the horse's breathing duration (inspiratory and expiratory time) and the limitations thereof as a function of forelimb anatomy and front leg stance time and/or stance distance during exercise had not been examined.

In the 1980's D. P. Attenburrow et al. developed a device for recording sound over the trachea which included a radio stethoscope and a spectrogram analysis of inspiratory and expiratory sounds of exercising horses. Later, however, it was found that sounds recorded in such a manner do not necessarily directly relate to the respiratory sounds of the exercising horse, see, e.g., Derksen et al. "Spectrogram Analysis of Respiratory Sounds in Exercising Horses", AAEP Proceedings, Vol. 45, pp.314–15 (1999) (Incorporated herein by reference). See also, "Spectrum analysis of respiratory sounds in exercising horses with experimentally induced laryngeal hemiplegia or dorsal displacement of the soft palate", AVJR Vol 62, No. 5, pp 659–664 (May 2001).

Derksen et al. advocate the use of a large and cumbersome recording device which can be placed alongside a horse exercising on a treadmill to pick up normal as well as abnormal respiratory sounds and assess pathology of the upper airway based upon the sound patterns produced during exercise, e.g., for detection of laryngeal hemiplegia and dorsal displacement of the soft palate. Derksen's analytical system, however, is limited in that it cannot be used on a galloping horse under field conditions (e.g., on a horse carrying an exercise rider or jockey and e.g., breezing or working) on a training track. Moreover, Derksen et al. did not examine or disclose any relationship between breathing duration, stance time and speed (velocity) and its effects on athletic potential or performance in the racing animal. Thus, there still exists a need in the art for a device and method which enables analysis of such parameters in the equine athlete, especially under field conditions.

Prior to the present invention, there has been no relationship established between front leg (or forelimb) stance time (or stance distance), speed (velocity), inspiratory and expiratory times and stamina (e.g., involuntary fatigue) which would be useful in predicting racing performance. Accordingly there still exists a need in the art for a method for predicting racing performance in racehorses which utilizes such factors.

OBJECTS OF THE INVENTION

It is an object of the invention to provide a method for predicting racing performance and/or identify performance limitations in a horse, e.g., a Thoroughbred, Arabian, Standardbred, Quarter Horse, Racing Paint and the like by measuring expiratory and/or inspiratory times during exercise.

It is also an object of the invention to provide a method for establishing the relationship between measured expiratory and/or inspiratory times during exercise to front leg stance time or stance distance and/or velocity in the prediction of racing performance in a racehorse.

A further object of the invention is to provide a consistent, reliable and reproducible method for determining that special or substantially ideal "speed" (maximum comfortable velocity) at which a particular horse can both run and still breath sufficiently and thereby delay the onset of involuntary fatigue (e.g., fatigue induced via hypoxia and/or lactic acidosis).

Yet another object of the invention is to provide a method for relating the anatomical constraints (the anatomy and/or conformation) of a particular individual horse's forelimb (e.g., a Thoroughbred horse) to that horse's available forelimb stance time or forelimb stance distance and further relate such information to that special or substantially ideal "speed" (maximum comfortable velocity) at which a particular horse can both run and still breathe sufficiently and thereby utilize such as a predictor of potential racing performance of the horse.

SUMMARY OF THE INVENTION

The present invention provides a method for predicting racing performance in a horse, e.g., a Thoroughbred race horse, comprising measuring expiratory and/or inspiratory times for a subject horse during exercise and relating such information to anatomy, front leg stance times and/or front leg stance distances and/or to speed (velocity) to determine the animal's potential to sustain a superior rate of ground coverage for a desired amount of time and identify a maximum comfortable velocity for the animal. A presently preferred embodiment of the methods of the invention comprises predicting performance via identification of expiratory time determined directly from the analysis of recorded respiratory sound from the exercising animal. The inspiratory and expiratory times can be measured directly from analysis of the amplitude envelope of the recorded sound using spectrogram analysis or other suitable computer software. A maximum comfortable velocity can be determined from expiratory time and velocity and performance predictions made.

The invention also provides a device for attachment to the head of a horse to enable recording of respiratory sounds in the intensely exercising animal, e.g., in a breezing Thoroughbred racehorse. In the presently preferred embodiment, the device is a lightweight blinkers-like hood which is placed on the subject horses head. The device is made to fit snugly over the face and comprises a pouch or closeable pocket located on the front of the hood for removable placement of a recording device. A thin shaft extends distally down the midline and over the bridge of the nose to a point just slightly in front of the tip of the horse's nose to carry the recording microphone.

DETAILED DESCRIPTION OF THE INVENTION

Figure 1:
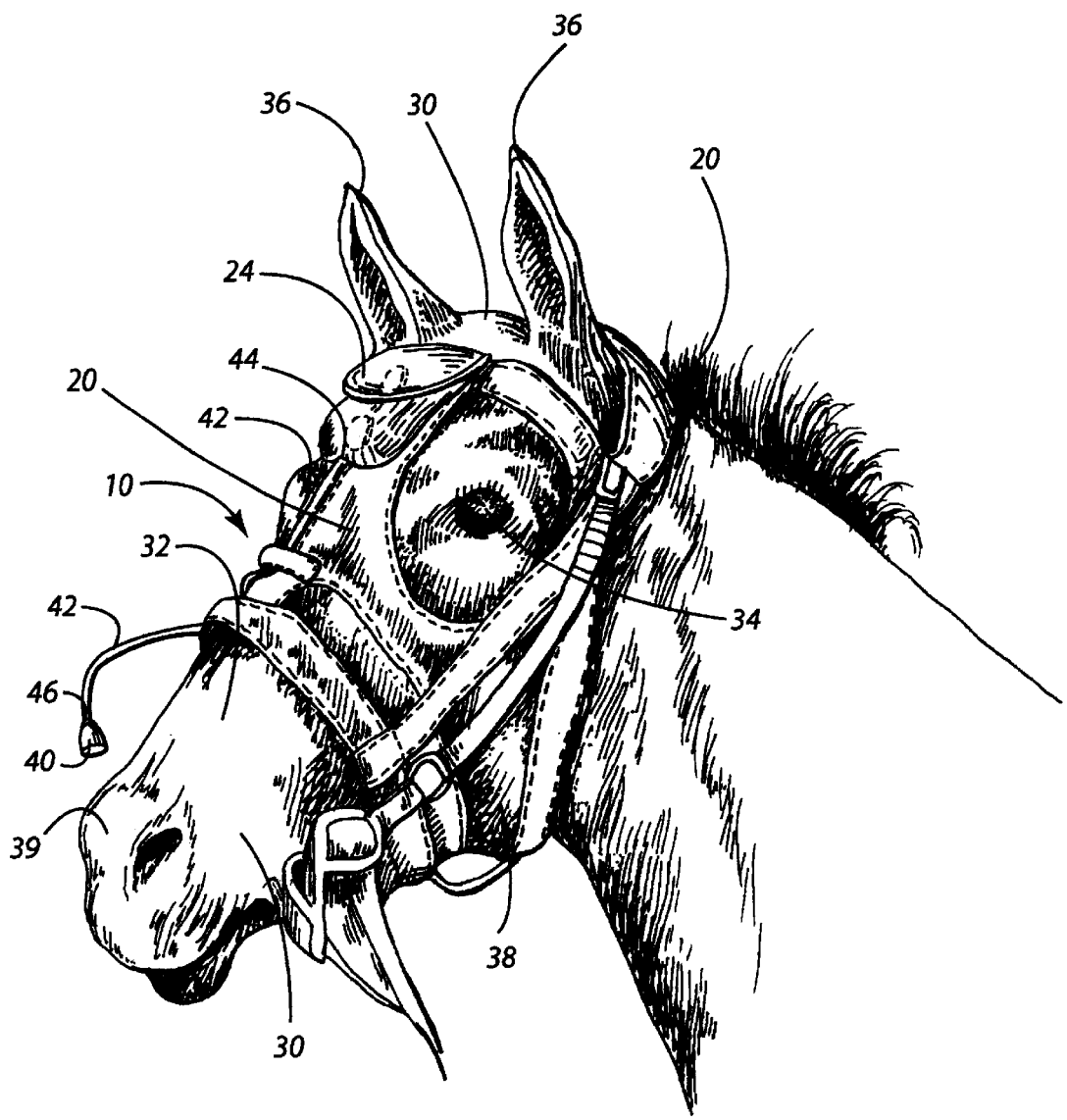
FIG. 1 is a perspective view of the device of the invention for recording respiratory sounds from a horse shown attached to the head of a horse.

Prior to the instant invention, there has been no functional relationship established between a horse's anatomy, especially forelimb anatomy, and the ability to properly inhale and exhale while running at a maximum or near maximum speed. The concept of relating a horse's front leg stance time and/or front leg stance distance to speed and ability to breath properly (to inhale and exhale properly) as a predictor of athletic potential has not been previously examined. Likewise, prior to the present invention, there was lacking a method for predicting athletic potential in horses utilizing analysis of recorded respiratory sounds to identify expiratory time (ET) and maximum comfortable velocity (MCV).

The present invention provides the novel discovery that as a galloping horse's speed generally increases his/her expiratory time can begin to place a limitation on the inspiratory time and/or inspiratory volume and eventually adversely affect the horse's performance. Generally speaking, at a gallop, the horse's maximum available expiratory time is defined as a function of the horse's front leg (forelimb) anatomy. In particular, the present invention provides the novel discovery that anatomical conformation of the equine forelimb dictates a maximum or substantially maximum available front leg stance time and/or front leg stance distance. Front leg stance time and/or stance distance, in turn, places a substantial functional limitation on available expiratory time. And, in general, a lower available expiratory time (e.g., due to poor conformation) can limit inspiratory time and/or inspiratory volume which can adversely affect racing performance. Thus, as the horse increases speed and loses the ability to properly breathe out (exhale) due to decreasing stance times, then he/she cannot properly breathe in (inhale) and performance is limited. Horses with proper forelimb conformation can sustain a minimally acceptable forelimb stance time at faster rates of speed and thereby out perform a poorly conformed counterpart. The present invention provides a device and method for analysis and identification of the superior performing individual.

Set forth in greater detail below are specific details related to novel methods for predicting racing performance in racehorses. The examples set forth herein are in no way intended to limit the scope of the invention. Those of skill in the art will realize that, given the teachings provided herein, many variations of the methods are possible that will fall within the scope of the general concept that it is now possible to predict racing potential and/or limitations thereof utilizing a combination of factors which include, but are not limited to, inspiratory and/or expiratory times, front leg stance time and/or front leg stance distance, and velocity (speed).

Thus, in one embodiment, the present invention provides a method for predicting racing performance in a horse, e.g., a Thoroughbred, Arabian, Standardbred, Quarter Horse or the like, comprising measuring expiratory and/or inspiratory times during exercise and relating such information to anatomy, front leg stance times and/or front leg stance distances and/or to speed (velocity) to determine the animal's potential to sustain a superior rate of ground coverage for a desired amount of time (e.g., a six furlong race) and thereby excel at racing. While the methods and general concepts disclosed herein are particularly useful for predicting racing performance in Thoroughbred race horses, one of ordinary skill in the art can appreciate that the methods set forth herein can be utilized to predict racing performance on other breeds of racehorses including, but not limited to Arabian, Quarter Horse, Standardbred, Racing Paints and the like.

When a horse gallops or runs, it normally breaths in a rhythm of inhalation and exhalation which is in relation to the horse's stride. The normal galloping horse will usually take one breath with each full stride, exhaling or breathing out during that period of the stride when its front legs are on the ground. The force generated when the front legs strike the ground aids in compressing the upper abdomen and thereby assisting in evacuating (expiring or exhaling) air from the lungs. See, "Respiration and Locomotion", *Equine Exercise Physiology*, pp 17–22 (1984) which is incorporated herein by reference.

The period of time that elapses while a selected front leg (right or left) is in contact with the ground is known as the front leg (or forelimb) "stance time." The front leg (or forelimb) "stance distance" is defined as the distance a horse travels while a selected limb (right or left forelimb) is in contact with the ground. Another distance, the "overlapped distance" is that distance the horse travels while both front feet are in contact with the ground. Conformational anatomy determines or to some extent limits the animal's front leg stance time.

One step of the presently preferred method for prediction of performance comprises determining the forelimb stance time and/or forelimb stance distance for the subject horse at a preselected rate of speed (velocity) of the gallop. This can be accomplished in a variety of ways, but is most accurately done by actually measuring the distance the horse travels while the horse's front foot (left and/or right) is in contact with the ground. The horse can be video taped during the gallop or exercise event such that frame speed and the like can be used to exactly measure distance or amount of ground covered while a selected front is in contact with the ground and thus the stance time can be accurately determined.

Another method for determining forelimb stance time is disclosed herein. In particular, the present invention provides a device and method for determining forelimb stance time in a galloping racehorse (e.g., under field conditions), comprising analyzing the racehorse's breathing pattern during exercise.

The presently preferred method comprises positioning a microphone at a desired location on the horse or near the horse which is capable of picking up sound emitted from the horse as he/she breathes during exercise. The microphone can be any of a variety of small portable microphones that are commercially available. For example, a presently preferred microphone is the ATR-35s Lavalier microphone manufactured by AUDIO-TECHNIA® of Stow, Ohio. This particular microphone is omnidirectional with an available frequency range of about 50–18,000 Hz, sensitivity of about −54 dBm±3 dB, 1 kHz at 1 Pa, and with an impedance of 1000 ohms±30%.

The microphone is attached to a portable recording device, e.g., a portable (micro) cassette recorder or digital recorder, and the recorder is, in turn, mounted on the horse or the rider as desired. Examples of presently preferred recording devices include the Sony® standard VOR micro cassette recorder, Model M-950 with detachable speaker and the Sony® Digital "MD" (MiniDisc) Model MZ-R70 Walkman®. The mini disc, for example, has a frequency response from about 20 to about 20,000 Hz±3 dB.

Alternatively, it is contemplated that the portable microphone can be connected to a telemetry device which is capable of transmitting the breathing sounds picked up by the microphone to a remote receiving unit for recording and analysis thereof, e.g., by means of a transmitted radio frequency signal. If desired, the sound or signal picked up by the microphone can be digitized prior to transmission by a portable unit mounted on the horse or transmitted to a remote unit and then digitized or otherwise processed for analysis.

One embodiment of the invention provides a device for attaching the recording device and microphone to the subject horse. In the presently preferred embodiment, the device is a lightweight hood or garment (similar to a traditional "blinkers" device commonly used in horse racing) which placed on the subject horses head. The device is made to fit snugly over the face (forehead and bridge of the nose) having a band of material extending from the bridge of the nose dorsally over the poll (just behind the ears) with holes cut out for the ears and eyes. The garment wraps around the face and head and is attached via a hook and loop type fastener, e.g., VELCRO® at the throat latch. A pouch or closeable pocket is located, on the front of the garment for removable placement of the recording device. It is desired that the pouch be located on the midline of the horse's forehead between and slightly anterior or dorsal to the horse's eyes so as not to interfere with the field of vision while the horse is exercising. Suitable materials for the hood or garment of the invention include, but are not limited to nylon, cloth or other suitable lightweight fabrics.

In one embodiment the desired location for placement of the microphone is just anterior or in front of the horses' nostrils. Accordingly, the presently preferred embodiment of the device of the invention comprises a mounting apparatus for the microphone which is comprised of a thin shaft removably attachable at its proximal end to the face of the garment that extends distally down the midline and over the bridge of the nose to a point just slightly in front of the tip of the horse's nose, preferably between about ¼ inch and about 6 inches but especially about 1–2 inches in front of the nose.

The aforementioned microphone is mounted at the distal end of the shaft. The wire for the microphone (if necessary) can be carried within the body of the shaft or wound around the exterior of the shaft extending up to the proximal end and attaching to the recording device. It can be appreciated that the shaft must be of sufficient stiffness to hold the microphone firmly in position during the exercise event. Likewise, it is desired that the shaft be of a low profile so as not to interfere with or distract the subject animal during exercise. Suitable materials for the shaft include, but are not limited to steel, metal alloys, plastics, polymer materials and the like. It is desirable that the shaft be adjustable in length to and bendable so as to be adaptable for use in different sized horses, with sufficient stiffness to carry the microphone in a stable position in front of the horse's nose.

As shown in FIG. 1, the device 10 of the invention is removable lightweight hood 20 which is placed on the subject homes head 30. The device 10 is made to fit snugly over the face, namely the forehead and bridge of the nose 32 with holes cut out for the ears 36 and eyes 34. The hood 20 wraps around the face and bead and is removably attachable via a hook and loop type fastener, e.g., VELCRO® (not shown) at the throat latch 38 of the horse. A pouch 24 (or closeable pocket) is located on the front of the hood 20 for removable placement of the recording device (not shown). It is desired that the pouch 24 be located on the midline of the horse's forehead between and slightly anterior or dorsal to the horse's eyes 34 so as not to interfere with the field of vision while the horse is exercising.

The device 10 further comprises a mounting apparatus for the microphone 40 which is comprised of a thin shaft 42 removably attachable at its proximal end 44 to the face of the hood 20 and extending distally down the midline and over the bridge of the nose 32 to a point just slightly in front of the tip of the horse's nose 39. Microphone 40 is mounted at the distal end 46 of the shaft 42. The wire for the microphone and or an antenna (if necessary) can be carried within the body of the shaft 42 or wound around the exterior of the shaft extending up to the proximal end 44 for attachment to the recording device (not shown). It can be appreciated that the shaft must be of sufficient stiffness to hold the microphone firmly in position during the exercise event. As shown in FIG. 1, it is desirable that the shaft 42 be adjustable in length and bendable so as to be adaptable for use in different sized horses, but with sufficient stiffness to carry the microphone in a stable position in front of the horse's nose 39.

In use, the hood, with the recording device and microphone attached, is placed on the subject horse's head and the horse is then asked to perform a desired exercise routine. Generally the horse is trotted or jogged a sufficient distance as a warm up before it is asked to gallop or breeze. A recording is made of the respiratory sounds emitted during the exercise event and preserved for analysis. Likewise, the subject animal's speed is recorded and, if desired, a video tape of the exercise event is made which can later be correlated with the sound recording and velocity in calculating stance time and/or stance distances, expiratory time (ET) and maximum comfortable velocity (MCV) as set forth more fully below.

Specially adapted computer software is utilized for analysis of the recording. In one embodiment, "Spectrogram" software (available from R. S. Horne at www.monumental.com/rshone/gram.html) is utilized for analysis of the recorded sound. This program provides a visual graph of the recorded sound which plots frequency range against time. The typical display band of frequencies ranges from about zero Hz to about 6,000 Hz. Exhalation sounds are generally seen at the lower end of the spectrum and are typically in the lower frequency ranges e.g., from less than about 2 kHz and especially less than about 1 kHz. Inspiratory sounds typically extend into the higher frequency ranges e.g., above about 2 kHz up to about 6 kHz. Using the presently preferred Spectrogram software, the recorded sound is analyzed and inspiratory and expiratory times are carefully measured. From this analysis, front leg stance times can be calculated.

After determination of the aforementioned stance times and/or stance distances from analysis of the recorded sound from the exercise event and/or from the analysis of the video or actual distances recorded from the exercise surface or a combination thereof, the method can further comprise a determination of the horse's expiratory time (ET), e.g., the amount of time for exhalation, according to the following formula:

$$ET = \left(\frac{\text{stance distance } LF}{V} + \frac{\text{stance distance } RF}{V}\right) - \frac{\text{overlapped distance}}{V}$$

Where ET=expiratory time, stance distance LF=the distance the horse travels while the left front foot is on the ground, stance distance RF=the distance the horse travels while the right front foot is on the ground, V=the relative velocity of the horse and overlap distance is the distance the horse travels, if any, while both his left front foot and right front foot are on the ground.

As provided by the present invention, the time with which a horse can breathe out or exhale (the ET) is limited by the range of movement in his front leg and especially the amount of time that the front limbs are in contact with the ground. Thus, as front leg stance time increases so does the amount of time which is available for proper exhalation.

Likewise, the velocity or speed at which the horse is traveling will affect the ET. The greater the velocity or rate of speed, the shorter the available ET. From the above formula, one of skill in the art will appreciate that, in general, the horse with an inherently longer front leg stance time and stance distance (e.g., due to superior front leg conformation) will cover a greater distance at a greater velocity with an increased ET. However, as velocity or speed increases for a constant or substantially constant stance time, the ET will decrease.

Under normal circumstances, the typical galloping, but not stressed horse will have an expiratory time which ranges from between about 0.2 to about 0.5 seconds and an inspiratory time which ranges from about 0.2 to about 0.5 seconds. One of skill in the art can appreciate that these ranges can vary depending upon the age of the animal, the speed of the gallop, length or duration of the gallop, stride length and the like. As provided by the invention, the critical minimal ET thought to be necessary to allow for proper breathing and ventilation is between about 0.17 and about 0.24 seconds, but especially about 0.20 seconds. In the galloping or racing animal, whenever ET times fall below about 0.18 seconds, the animal can no longer breath properly and the metabolic consequences associated therewith will quickly ensue and the animal will be forced to slow down.

In other words, as the horse goes faster his breathing times will change such that his expiratory times decrease until they reach a critical point. At that moment, the horse will be incapable of producing enough air flow to meet its metabolic demands and shortly thereafter it will have to slow down. Thus, the present invention also provides a method for determining the substantially ideal velocity or "speed" at which a particular horse can both run and still breathe sufficiently, namely the Maximum Comfortable Velocity (MCV). Beyond that speed, breathing times, especially ET will be inadequate to support competitive racing.

In a presently preferred embodiment the invention provides a method of predicting racing performance in a horse comprising calculating a maximum comfortable velocity (MCV) for the subject horse. The "maximum comfortable velocity" in general is meant to include a maximum or substantially maximum rate of speed or ground coverage (velocity) that a particular animal can sustain for a predetermined amount of time (e.g., the length of a preselected race) while still maintaining an allowable minimal or substantially minimal expiratory time. Thus, one of skill in the art can appreciate that a horse demonstrating a higher MCV is able to run faster and perform better than a counterpart demonstrating a lower MCV.

Alternatively, the ET or expiratory times can be evaluated and determined directly from the analysis of recorded respiratory sound from the exercising animal. The inspiratory and expiratory times can be measured directly from analysis of the amplitude envelope of the recorded sound using the spectrogram software or other suitable algorithms. Markers for certain events are identifiable in the breathing patterns of the recorded breathing sounds generated during exercise. Such markers include, but are not limited to the null sound between breaths at slower speeds, sharp frequency changes such as a dramatic increase in amplitude marking, e.g., the beginning of exhalation, variations in rate of change of amplitude, and the like.

EXAMPLE

FIGS. 2–5 are directed to the analysis of two thoroughbred race horses, Horse F-1 and Horse B-2, using the device and methods provided by the invention. In general, the device of the invention as shown in FIG. 1 and described above was attached to each horse and a recording was made of the subject horse's breathing sounds during a breeze (fast workout) over a dirt training track. The breeze or workout was also videotaped and times recorded for each furlong of the workout.

Horse F-1 is a Grade I stakes winning filly and Horse B-2, a colt, is a winner at the $5,000.00 claiming level, thus there is a vast difference in athletic ability of these two animals. The spectrogram analysis of the recorded breathing patterns of these two horses demonstrates the utility of the methods for predicting racing performance as set forth herein. As set forth in greater detail below, both horses demonstrate a pathogenic whistling sound during a workout (breeze) and endoscopic examination of the upper airway of both horses reveals an abnormal function to the larynx which would not pass a pre-purchase examination. Surprisingly, however, Horse F-1 is a multiple Grade 1 winner and, as is demonstrated by her racing performance and in the analysis set forth below, is able to overcome the pathological problems associated with her larynx due in part to her superior front leg stance times and therefore, extended or increased ET.

Figure 2:
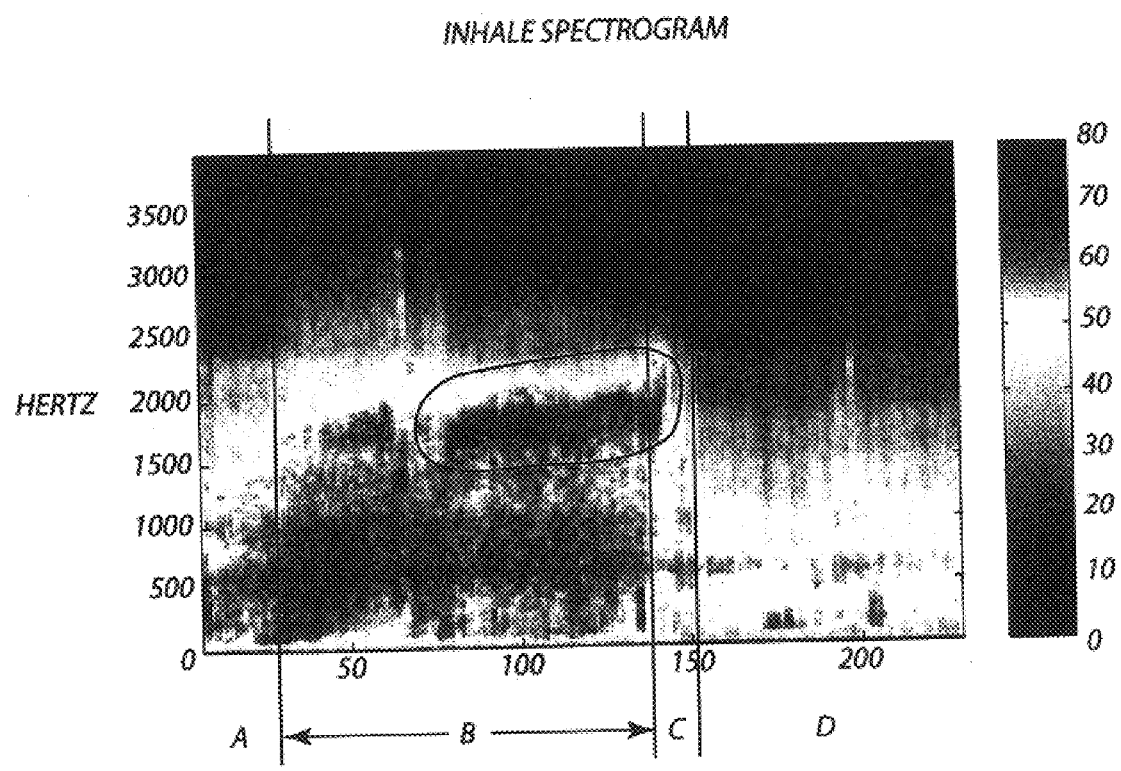
FIG. 2 is a graphic representation of a recording of respiratory sounds of an exercising horse.
Figure 3:
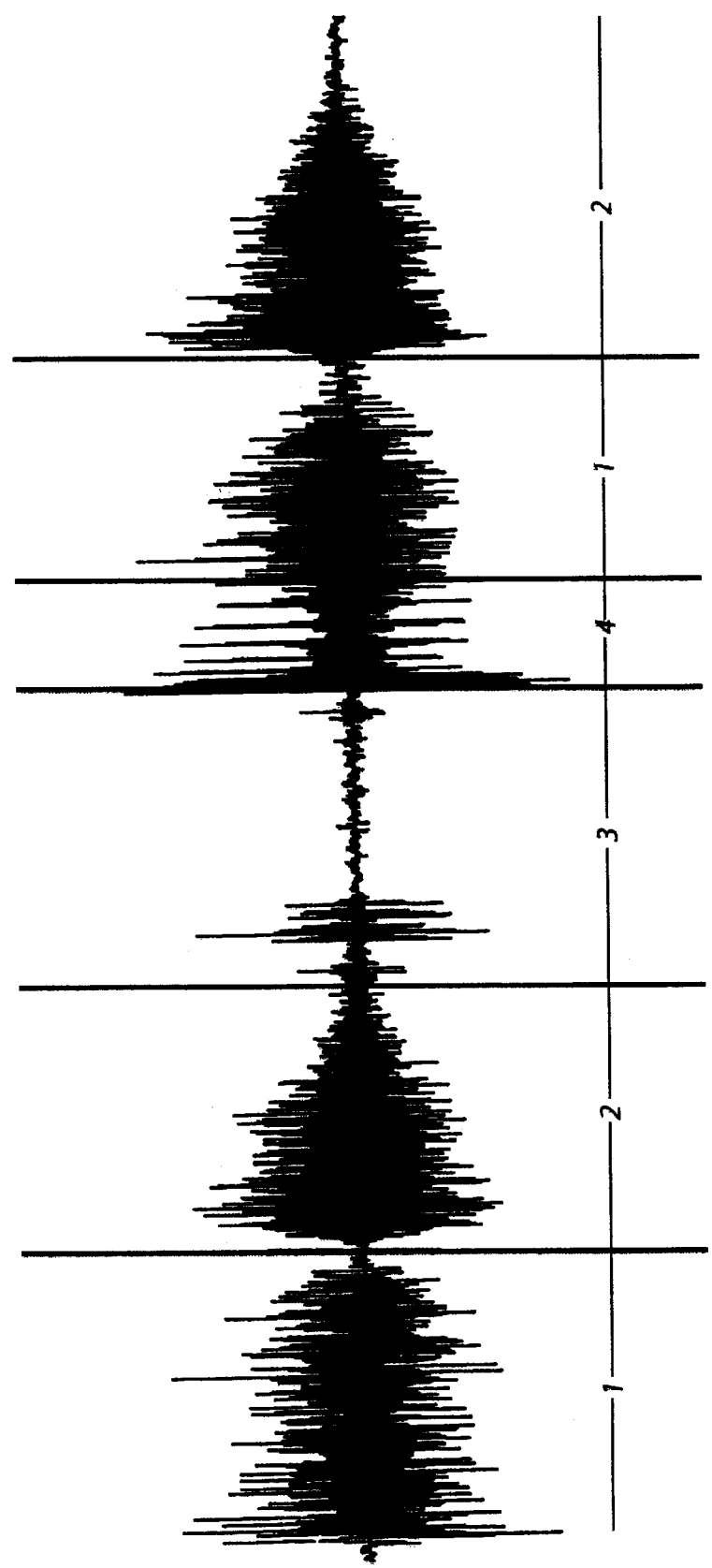
FIG. 3 is a graphic representation of a recording of respiratory sounds of an exercising horse.
Figure 5:
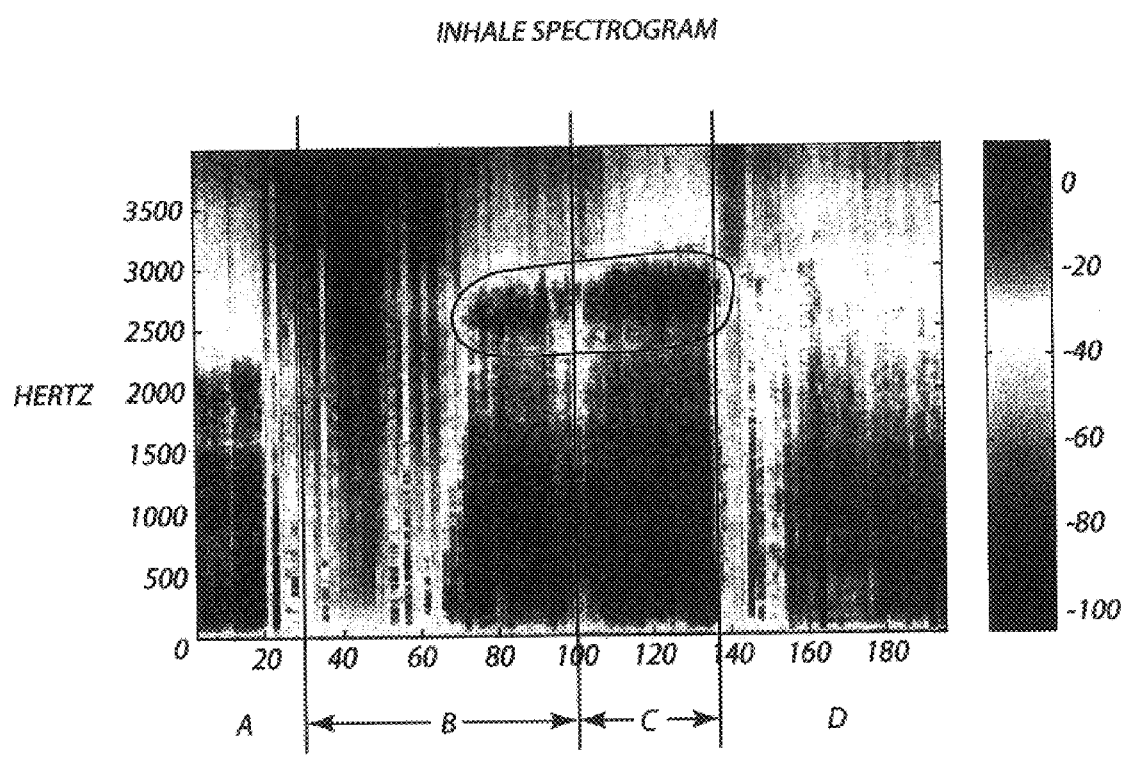
FIG. 5 is a graphic representation of a recording of respiratory sounds of an exercising horse.

In FIGS. 2, 3 & 5 the graphs shown are spectrograms of the exercise event shown with frequency shown on the vertical axis in Hertz and time shown on the horizontal axis. The recording and spectrogram shown starts roughly 30 seconds before the workout (breeze) begins and lasts until about 90 seconds after the end of the breeze. The area denoted in FIGS. 2 & 5 on the horizontal axis as A is the sound recorded of the subject horse at a gallop for approximately 30 seconds prior to the beginning of the breeze (workout). Area B denotes the actual breeze, area C denotes the gallop out at the end of the breeze as the horse is being pulled up, and area D denotes the recorded sound after the horse has pulled up, i.e, slowed to a walk.

As shown in FIG. 2, Horse F-1 has a steady and regular breathing pattern established at the gallop going into the beginning of the five furlong breeze (orange and red areas of the graph in area A from about zero to about 1500 Htz. This steady and regular breathing pattern is maintained throughout the breeze (area B) and the filly quickly returns to a normal resting breathing pattern (area D) following the breeze. The pathogenic whistle can be seen in area C within the encircled area in bright orange. Recorded fractions for the five furlong breeze were 13.8, 13.0, 14.3, 13.6, and 13.5 seconds per furlong respectively.

FIG. 3 shows an expanded view of the recorded sound of Horse F-1 after the breeze (workout) taken from area D of FIG. 2 with amplitude plotted on the vertical axis and time on the horizontal axis. Area 1 denotes an exhalation, area 2 denotes an inhalation, area 3 denotes a swallow, and area 4 denotes a palate flutter during exhalation.

Figure 4:
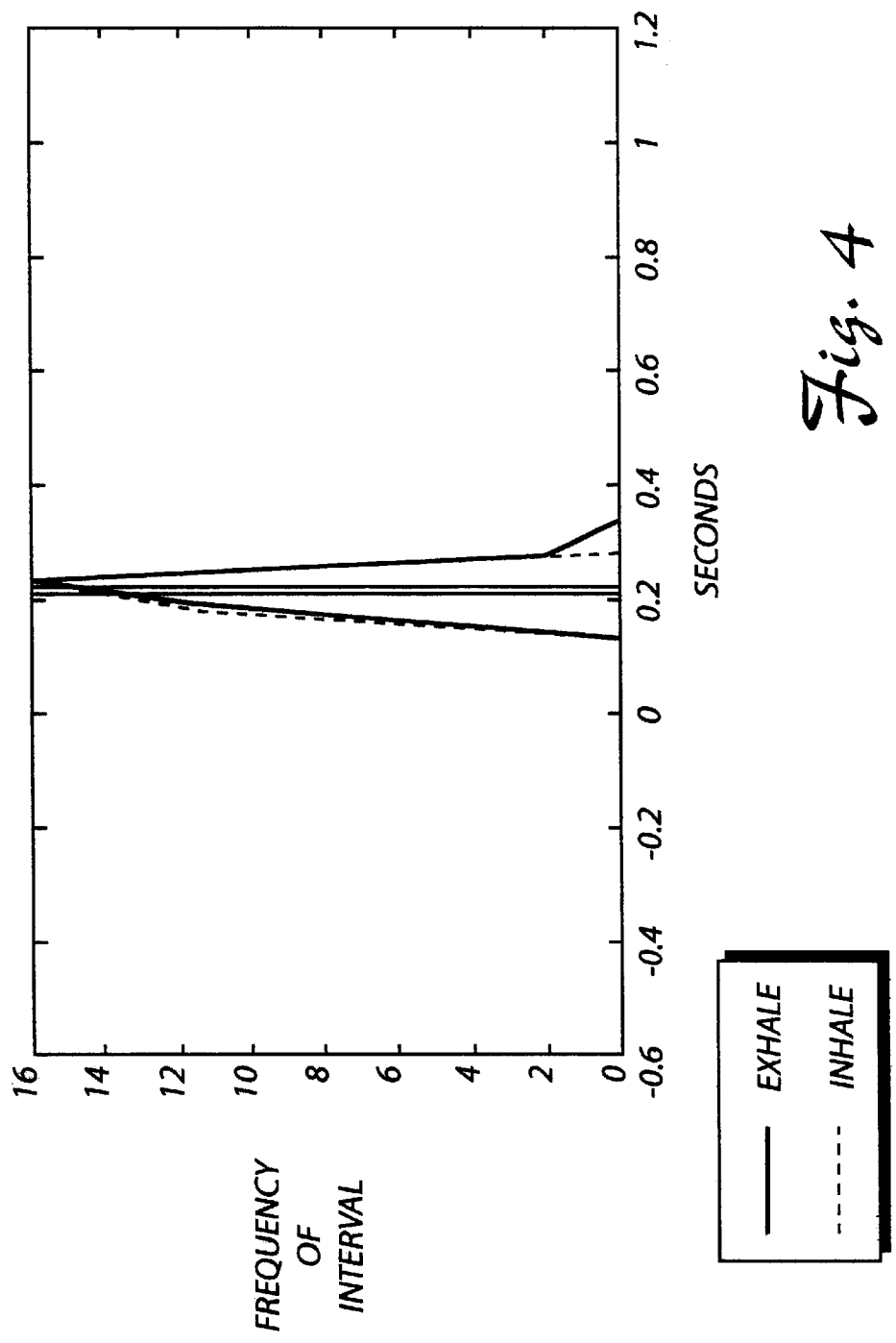
FIG. 4 is a graphic representation of the Distribution of Breath Cycles generated from a recording of respiratory sounds of an exercising horse.

FIG. 4 is a graphic representation of the average distribution of breath cycles for same filly, Horse F-1, breezing a furlong in 12.4 seconds. As can be seen from the graph, Horse F-1 is capable of maintaining an ET (expiratory time) of about 0.22 seconds for the duration of the workout and thus was traveling at less than her maximum comfortable velocity. Given the fact that this filly has a pathologic whistle during her works and demonstrable laryngeal pathology via endoscopic examination, it is surprising that this filly is capable of winning at the highest level of thoroughbred racing competition. The methods of the invention, however, reveal this filly's ability to maintain a sustained ET in the desirable range indicating that she has the ability to breeze at levels typical of Grade I horses without reaching her MCV.

Horse F-1 is a sharp contrast to the $5.000.00 claiming winner, Horse B-2, whose workout (breeze) is depicted in FIG. 5. Area A of FIG. 5 shows a breathing pattern at the gallop for Horse B-2 which is very similar to that shown for Horse F-1 in FIG. 2. At the start of the four furlong breeze, Horse B-2 breathes erratically and ends the breeze (area B) with a distinctly noticeable pathologic whistle (shown in orange in the circled area) which extends well into the gallop out, area C. Horse B-2 continues to breathe heavily after being pulled up, area D. Horse B-2 worked the first furlong in 12.4 seconds and the second furlong in 12.1 seconds which exceeded his maximum comfortable velocity (MCV) and he therefore was forced to slow down, working the third furlong in 13.6 seconds.

Horse B-2 demonstrated a reduced ET at furlong speeds of 12.4 and 12.1 seconds as well as a pathological whistle and accordingly, as born out by his racing performance, would not be a good candidate for selection when applying the methods of the invention. This is contrasted to Horse F-1 (a Grade I winner) which would not have been selected as a superior athlete based upon prior art criteria (would not pass a pre-purchase evaluation of the upper airway (endoscopic exam)), however, she is seen, as shown above as a horse with great potential when the methods of the invention are utilized for evaluation, not withstanding her pathological whistle.

Additional objects, advantages and other novel features of the invention will be set forth in part in the description that follows and in part will become apparent to those skilled in the art upon examination of the foregoing or may be learned with the practice of the invention.

The foregoing description of a preferred embodiment of the invention has been presented for purposes of illustration and description. It is not intended to be exhaustive or to limit the invention to the precise form disclosed. Obvious modifications or variations are possible in light of the above teachings. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally and equitably entitled.

What is claimed is:

1. A device for recording respiratory sound in an exercising horse, comprising a hood designed for removable attachment to the head of the exercising horse, the hood further comprising means for carrying a removable recording device thereon and means for positioning a recording microphone at a desired location adjacent the nose of the exercising horse.

2. The device of claim 1 wherein the carrying means for the removable recording device is a pouch located at a preselected spot on the hood.

3. The device of claim 2, wherein the hood is a blinkers-type hood having a forehead piece and the preselected location of the pouch is on the forehead piece.

4. The device of claim 3, wherein the recording microphone positioning means further comprises a hollow thin shaft having a proximal end extending from the pouch and a distal end adapted for attachment of a recording microphone.

5. The device of claim 4, further comprising a recording microphone located at the distal end of the hollow thin shaft and a removable recording means contained within the pouch and wherein the recording microphone is connected to the removable recording means via an electrical wire traveling through the hollow thin shaft.

6. The device of claim 1, wherein the recording microphone is located a preselected distance in front of the nose of the exercising horse.

7. A method for predicting potential performance in a selected racing or training animal, comprising analyzing respiratory sound from the selected animal during an exercise event wherein the analyzing step comprises calculating an average expiratory time for the selected animal during the exercise event at a known velocity over a preselected distance to determine a substantially maximum comfortable velocity for the selected animal.

8. A method for predicting potential performance in a selected racing or training animal, comprising analyzing respiratory sound from the selected animal during an exercise event, wherein the analyzing step comprises calculating an average inspiratory time for the selected animal during the exercise event at a known velocity over a preselected distance to determine a substantially maximum comfortable velocity for the selected animal.

9. The method of claim 3, wherein the animal is a horse.

10. The method of claim 9, wherein the horse is selected from the group consisting of a Thoroughbred, an Arabian, a Standardbred, and a Quarter Horse.

11. A method for predicting potential performance in a selected racing or training animal, comprising analyzing respiratory sound from the selected animal during an exercise event, wherein the analyzing step comprises calculating a substantially maximum comfortable velocity for the selected animal during the exercise event.

12. A method for predicting potential performance in a selected racing or training animal, comprising analyzing respiratory sound from the selected animal during an exercise event wherein, prior to the analyzing step, the method further comprises the steps of recording the respiratory sound from the selected animal; videotaping the exercise event and determining a velocity for the selected animal over a preselected distance.

13. The method of claim 12, further comprising the step of determining a front leg stance time of the selected animal over a preselected distance.

14. The method of claim 12, wherein the analyzing step comprises comparing a calculated average expiratory time for the selected animal during the exercise went at a known velocity over a preselected distance ascertained from analysis of the recorded respiratory sound with an actual average stance time and actual expiratory time as determined from a videotape of the exercise event.

15. The method of claim 5, wherein the recorded respiratory sound is analyzed by evaluation of frequency and amplitude of the recorded respiratory sound.

16. The method of claim 15, wherein the recorded respiratory sound is analyzed via spectrogram computer software.

* * * * *

UNITED STATES PATENT AND TRADEMARK OFFICE
CERTIFICATE OF CORRECTION

PATENT NO. : 6,602,209 B2
DATED : August 5, 2003
INVENTOR(S) : David H. Lambert and Deborah A. Boehler It is certified that error appears in the above-identified patent and that said Letters Patent is hereby corrected as shown below:

<u>Column 6,</u>
Line 36, replace "homes" with -- horses --

Signed and Sealed this

Twenty-first Day of October, 2003

JAMES E. ROGAN
*Director of the United States Patent and Trademark Office*